US005702729A

United States Patent [19]
Fitzgerald

[11] Patent Number: 5,702,729
[45] Date of Patent: Dec. 30, 1997

[54] METHODS FOR THE PREVENTION AND TREATMENT OF GASTROINTESTINAL DISORDERS CAUSED OR MEDIATED BY ALGAE OR CYANOBACTERIA

[75] Inventor: Jamesina Anne Fitzgerald, Hamilton, Ohio

[73] Assignee: The Procter & Gamble Company, Cincinnati, Ohio

[21] Appl. No.: 569,028

[22] Filed: Dec. 7, 1995

[51] Int. Cl.$^6$ .................. A61K 33/24; A61K 31/28
[52] U.S. Cl. .................. 424/653; 514/492; 514/867
[58] Field of Search .................. 424/653; 514/492, 514/867

[56] References Cited

U.S. PATENT DOCUMENTS

| | | | |
|---|---|---|---|
| 4,049,817 | 9/1977 | Laber et al. | 424/270 |
| 4,514,421 | 4/1985 | Herschler | 418/110 |
| 5,221,664 | 6/1993 | Berkowitz et al. | 514/6 |
| 5,256,684 | 10/1993 | Marshall | 514/398 |

FOREIGN PATENT DOCUMENTS

| | | | |
|---|---|---|---|
| 962163 | 6/1950 | France | |
| 63-174926 | 7/1988 | Japan | A61K 31/29 |
| WO 92/01457 | 2/1992 | WIPO | A61K 33/24 |
| WO 95/32720 | 12/1995 | WIPO | |

OTHER PUBLICATIONS

Cavier, R., "Etude des propriérés parasiticides de quelques complexes bismuthiques de l'oxy-8 quinoléine", Annales pharmaceutiques francaises, 1973, 31, No. 4, pp. 173–178 (translation attached).

Pitlik, S., et al., "Cryptosporidial Cholecystitis", The New England Journal of Medicine, vol. 308, No. 16 (Apr. 21, 1983), p. 967.

Than, U Pe, et al., "The Alkaloids of Holarrhena Antidysenterica", Union of Burma Journal of Science and Technology, vol. 2, Dec. 1969, pp. 423–436.

Chevalier, C., et al., "Bilan Des Antiparasitaires A Usage Veterinaire: Antihelminthiques, Anticoccidiens, Antifongiques, Ectoparasiticides" (translation attached), Laboratory of Therapeutic Chemistry, College of Pharmacy, 37042 Tours Cedex, pp. 624–630.

DuPont, H., et al., "Symptomatic Treatment of Diarrhea With Bismuth Subsalicylate Among Students Attending a Mexican University", Gastroenterology, vol. 73, (1977), pp. 715–718.

DuPont, H., "Enteropathogenic Organisms: New Etiologic Agents and Concepts of Disease", Medical Clinics of North America, vol. 62, No. 5, (1978), pp. 945–960.

Wolfe, M., "The Treatment of Intestinal Protozoan Infections", Medical Clinics of North America, vol. 56, No. 3 (1982), pp. 707–720.

Journal of the American Medical Association, "Travelers' Diarrhea", vol. 253, No. 18 (1985), pp. 2700–2704.

DuPont, L., "Nonfluid Therapy and Selected Chemoprophylaxis of Acute Diarrhea", The American Journal of Medicine, vol. 78, Suppl. 6B (1985), pp. 81–90.

Johnson, P., et al., "Comparison of Loperamide With Bismuth Subsalicylate for the Treatment of Acute Traveler's Diarrhea", The Journal Of the American Medical Association, vol. 255, No. 6 (1986), pp. 757–760.

Steffen, R., "Anerkannte Prinzipien zur Prophylaxe und Therapie der Reisediarrhoe", Schweiz. med. Wschr. 116, Nr. 20 (1986), pp. 670–673 (translation provided).

DuPont, H., et al., "Prevention of Travelers' Diarrhea By the Tablet Formulation of Bismuth Subsalicylate", The Journal of the American Medical Association, vol. 257, No. 10 (1987), pp. 1347–1350.

White, N., "Drug Treatment and Prevention of Malaria", European Journal of Clinical Pharmacology, vol. 34 (1988), pp. 1–14.

D'Alessandro, A., "Amebiasis Then", American Journal of Tropical Medicine and Hygiene, vol. 41, No. 3, Suppl. (1989), pp. 38–39.

Steffen, R., "Worldwide Efficacy of Bismuth Subsalicylate in the Treatment of Travelers' Diarrhea", Reviews of Infectious Diseases, vol. 12, Suppl. 1 (1990), pp. S80–S86.

Long, E., et al., "Alga Associated with Diarrhea in Patients with Acquired Immunodeficiency Syndrome and in Travelers", Journal of Clinical Microbiology, vol. 28, No. 6 (1990), pp. 1101–1104.

Wolfe, M., "Acute Diarrhea Associated With Travel", The American Journal of Medicine, vol. 88, Suppl. 6A (1990), pp. 34S–37S.

Qadri, S.M.H., "Infectious Diarrhea: Managing a Misery that is Still Worldwide", Postgraduate Medicine, vol. 88, No. 5 (1990), pp. 169–184).

Farthing, M.J.G., et al., "Treatment and Prevention of Travellers' Diarrhoea", Gastroenterology International, vol. 5, No. 3 (1992), pp. 162–175.

Zinsser Microbiology, 20th ed., Appleton & Lange (1992), pp. 1161–1173.

Arduino, R., et al., "Travellers' Diarrhoea", Bailliere's Clinical Gastroenterology, vol. 7, No. 2 (1993), pp. 365–385.

Chak, A., et al., "Traveler's Diarrhea", Gastroenterology Clinics of North America, vol. 22, No. 3 (1993), pp. 549–561.

American Health Consultants, "Cryptosporidiosis in Milwaukee", vol. 12, No. 15 (1993), pp. 113–115.

Wittner, M., et al., "Parasitic Infections in AIDS Patients: Cryptosporidiosis, Isosporiasis, Microsporidiosis, Cyclosporiasis", Infectious Disease Clinics of North America, vol. 7, No. 3 (1993), pp. 569–586.

Weber, R., et al., "Disseminated Microsporidiosis Due to *Encephalitozoon Hellem*: Pulmonary Colonization, Microhematuria, and Mild Conjunctivitis in a Patient with AIDS", Clinical Infectious Diseases, vol. 17 (1993), pp. 415–419.

(List continued on next page.)

Primary Examiner—Kevin E. Weddington
Attorney, Agent, or Firm—Mary Catherine Poland; Douglas C. Mohl; Jacobus C. Rasser

[57] ABSTRACT

The subject invention encompasses methods for the prevention and treatment of a human or lower animal subject having a gastrointestinal disorder caused or mediated by algae and/or cyanobacteria comprising administering bismuth to the subject.

8 Claims, No Drawings

OTHER PUBLICATIONS

Kuhls, T., "Protozoal Infections of the Intestinal Tract in Children", Advances in Pediatric Diseases, vol. 8 (1993), pp. 177–202.

Scott, D., et al., "Treatment of Gastrointestinal Infections", Bailliere's Clinical Gastroenterology, vol. 7, No. 2 (1993), pp. 477–499.

Martindale, The Extra Pharmacopeia, "Gastro–intestinal Agents", Thirtieth Ed., The Pharmaceutical Press (1993), p. 872.

Health, "Are Milwaukee–Type Parasites Floating in My Drinking Water?" (1993), p. 14.

Sun, T., et al., "Intestinal Microsporidiosis: Report of Five Cases", Annals of Clinical and Laboratory Science, vol. 24, No. 6 (1994), pp. 521–532.

American Drug Index, 38th Ed. (1994), pp. 568–569.

Upcroft, P., "Multiple Drug Resistance in the Pathogenic Protozoa", Acta Tropica, vol. 56 (1994), pp. 195–212.

Herwaldt, B., et al., "Infections with Intestinal Parasites in Peace Corps Volunteers in Guatemala", Journal of Clinical Microbiology (1994), pp. 1376–1378.

Physicians'Desk Reference, 48th Ed. (1994), pp. 724–726.

Jernigan, et al., "Parasitic Infections of the Small Intestine", Gut, vol. 35, No. 3 (1994), pp. 289–293.

Fritsche, T., et al., "Introduction to Diagnostic Parasitology: Biologic, Clinical, and Laboratory Considerations", Manual of Clinical Microbiology, Sixth Ed., ASM Press (1995), pp. 1141–1144.

METHODS FOR THE PREVENTION AND TREATMENT OF GASTROINTESTINAL DISORDERS CAUSED OR MEDIATED BY ALGAE OR CYANOBACTERIA

BACKGROUND OF THE INVENTION

While bacteria and viruses have long been recognized as a leading cause of diarrhea and other gastrointestinal illness throughout the world, it was not until recently that cyanobacteria and algae have been considered in the etiology. Algal blooms are ocurring more often than before both in freshwater and coastal areas due to human-made changes in the environment. *Encyclopedia of Microbiology*, vol. 1, 68, (1992). Some of the bloom-forming algae produce toxic substances. These algae, which are ingested by mollusks and fish, may produce serious or even life-threatening illness when the fish and shellfish are consumed by humans. Id. In addition, species of cyanobacteria are becoming increasingly suspect for causing diarrhea and other gastrointestinal illness in healthy and immunocompromised subjects. Therefore, diarrhea and other gastrointestinal disorders associated with algae and/or cyanobacteria represent a serious health concern and the need for effective treatment therapies continues to grow.

It has been discovered by the present invention that the administration of bismuth salts may be effective for the prevention and/or treatment of gastrointestinal disorders caused or mediated by one or more organisms selected from the group consisting of algae, cyanobacteria, and combinations thereof. Thus, an object of the present invention is to provide a safe and effective method of preventing and/or treating gastrointestinal disorders caused or mediated by algae and/or cyanobacteria. A further object of the invention is to provide such a method comprising the administration of bismuth.

These and other objects of the present invention will become readily apparent from the derailed description which follows.

SUMMARY OF THE INVENTION

The present invention relates to a method for treatment of a human or lower animal subject having a gastrointestinal disorder caused or mediated by one or more organisms selected from the group consisting of algae, cyanobacteria, and combinations thereof, comprising administering to the subject from about 50 milligrams to about 5000 milligrams of bismuth, per day, for from about 1 to 56 days.

The present invention also relates to a method for prevention in a human or lower animal of a gastrointestinal disorder caused or mediated by one or more organisms selected from the group consisting of algae, cyanobacteria, and combinations thereof, comprising administering to the subject from about 50 milligrams to about 5000 milligrams of bismuth, per day, for from about 1 to 28 days.

DETAILED DESCRIPTION OF THE INVENTION

The methods of the present invention comprise the prevention and/or treatment of gastrointestinal disorder caused or mediated by one or more alga(e) and/or cyanobacteria. Such gastrointestinal disorders are prevented and/or treated by the administration of bismuth. The components of the present invention are more fully defined below.

Gastrointestinal Disorder

The term "gastrointestinal disorder", as used herein, encompasses any infection, disease or other disorder of body, typically of the upper and/or lower gastrointestinal tract, caused or mediated by one or more organisms selected from the group consisting of algae, cyanobacteria, and combinations thereof. Such disorders include one or more of the following conditions: diarrhea, abdominal pain and/or cramping, flatulence, nausea, abdominal distention, fever, constipation, blood, mucus and/or pus present in feces, vomiting, gastroenteritis, weight loss, anorexia, malaise, and any other condition commonly associated with infection by algae and/or cyanobacteria.

In immunocompromised subjects and children, gastrointestinal disorders caused or mediated by algae and/or cyanobacteria may be more severe and life threatening than the common disorders listed above. Therefore, the term "gastrointestinal disorder" also includes any condition commonly associated with algae and/or cyanobacteria infection in immunocompromised subjects and children, including but not limited to, acute diarrhea, dehydration, electrolyte imbalance, colitis, and fatal necrosis of the intestine.

Algae and Cyanobaeteria

Algae represent a large, heterogeneous group of primitive photosynthetic organisms which occur throughout all types of aquatic habitats and moist terrestial environments. Nadakavukaren et al., *Botany. An Introduction to Plant Biology*, 324–325, (1985). The term "algae", as used herein, refers to the following algal divisions: Chlorophyta (green algae), Euglenophyta (euglenoids), Chrysophyta (golden and yellow-green algae, diatoms), Phaeophyta (brown algae), Pyrrophyta (dinoflagellates), and Rhodophyta (red algae). Such divisions are described more fully in Nadakavukaren et al., *Botany. An Introduction to Plant Biology*, 324–349, (1985), Brock et al., *Biology of Microorganisms*, 815–817, (1991), and Bold et al., *Introduction to the Algae*, 1–32, (1978), which are incorporated herein by reference.

Green algae include Chlorella and Chlorococcum. Euglenoids include *Euglena mesnili*, *Trachelomonas armata*, and *Phacus pleuronectes*. Golden algae include Dinobryon, spp. and Synura, spp. Diatoms include *Nitzschia pungens, f. multiseries*, and *Nitzschia pseudodelicatissima*. Brown algae include *Pilayella littoralis* (zoospores). Dinoflagellates include *Dinophysis acuminata*, *Dinophysis norvegica*, Gymnodinium, and *Gonyaulax catenella*. Red algae include Rhoclymenia, spp. and Bangia, spp. Preferred algae are Chlorophyta such as Chlorella and Chlorococcum; Chrysophyta such as Dinobryon and Synura; and combinations thereof. Most preferred algae are Chlorophyta such as Chlorella and Chlorococcum.

The term "cyanobacteria", as used herein, refers to prokaryotic organisms formerly classified as the blue-green algae. Cyanobacteria are a large and diverse group of photosynthetic bacteria which comprise the largest subgroup of Gram-negative bacteria. Cyanobacteria were classified as algae for many years due to their ability to perform oxygen-evolving photosynthesis. Curtis, "Cyanobacteria, Molecular Genetics", *Encyclopedia of Microbiology*, vol. 1, 627 (1992). While many cyanobacteria have a mucilaginous sheath which exhibits a characteristic blue-green color, the sheaths in different species may also exhibit colors including light gold, yellow, brown, red, emerald green, blue, violet, and blue-black. Raven et al., *Biology of Plants*, Fourth Edition, 183–185, (1986), included herein by reference. Cyanobacteria include *Microcystis aeruginosa*, *Trichodesmium erythraeum*, *Aphanizomenon flos-aquae*, and *Anabaena flos-aquae*.

Diagnosis of gastrointestinal disorders caused or mediated by algae may be accomplished by any method commonly used in the medical community.

Bismuth

The methods of treatment and/or prevention in the present invention involve administration of bismuth. As used herein, the quantity of bismuth is by weight of elemental bismuth.

The preferred duration of bismuth administration will vary according to the specific gastrointestinal disorder to be treated and the physical condition of the subject being treated. In general, as a method of treatment, bismuth may be administered in an amount of from about 50 milligrams to about 5000 milligrams, and preferably from about 50 milligrams to about 2500 milligrams, per day, for from about 1 to about 56 days, preferably for from about 2 to about 28 days, and most preferably for from about 7 to about 21 days.

In general, as a method of prevention, bismuth may be administered in an amount of from about 50 milligrams to about 5000 milligrams, and preferably from about 50 milligrams to about 2500 milligrams, per day, for from about 1 to about 21 days, and preferably for from about 1 to about 14 days. In a method of prevention, bismuth may be administered prior to potential exposure to algae and/or cyanobacteria. Such administration of bismuth may vary depending on the likelihood of algae and/or cyanobacteria exposure and condition of the subject and may be commenced at any time deemed beneficial by the medical community including from about 1 to about 7 days, from about 2 to about 5 days, and from about 3 to about 4 days, prior to potential exposure.

In the present invention, the term "bismuth", as used herein, includes bismuth in the form of a pharmaceutically-acceptable salt, bismuth or bismuth salt in the form of an organic or other complex which contains bismuth as an active ingredient, and mixtures thereof. Such organic complexes include 2,2'-spirobi[1,3,2-benzodoxabismole]. Preferably, bismuth is administered in the present methods as a pharmaceutically-acceptable salt. Such bismuth salts include bismuth aluminate, bismuth subcarbonate, bismuth subcitrate, bismuth titrate, tripotassium dicitrato bismuthate, bismuth subgalate, bismuth subnitrate, bismuth tartrate, bismuth subsalicylate, and mixtures thereof. Bismuth titrate, bismuth subcitrate, tripotassium dicitrato bismuthate, bismuth tartrate, bismuth subsalicylate, and mixtures thereof are preferred bismuth salts for use in this invention.

The bismuth useful herein may be administered alone, or in combination with other pharmaceutically-acceptable components in a bismuth-containing composition. A variety of such compositions containing bismuth salts are commercially available. Such compositions include DeNol, containing tripotassium dicitrato bismuthate (by Brocades); Bislumina, containing bismuth aluminate (by Mazuelos); Roter, containing bismuth subnitrate (by Roterpharma); Devrom®, containing bismuth subgalate (by The Parthenon Co., Inc.); and Pepto-Bismol®, containing bismuth subsalicylate (by The Procter & Gamble Company).

As used herein, the term "administering" refers to any method which, in sound medical practice delivers the compounds or compositions used in this invention to the subject to be treated in such a manner so as to be effective in the treatment of the gastrointestinal disorder. Preferably, the bismuth is administered orally.

The following non-limiting examples illustrate the methods and uses of the present invention.

EXAMPLE I

A young boy suffers from abdominal cramps and painful acute diarrhea, following a swim in his family's pond. Fecal samples are taken from the subject and analyzed microscopically and via culture. There are no indications of bacterial infection. Likewise, there are no indications of intestinal protozoa or worms. Strangely, large numbers of green algae, determined to be Chlorococcum, are evident in the diarrheic stools. The young boy is treated by administering a composition containing bismuth subsalicylate, sold by The Procter & Gamble Company under the name "Pepto-Bismol®". The composition, in liquid form, is administered four times daily, in equal doses delivering approximately 2500 milligrams of bismuth per day, for 21 days. Thereafter, fecal samples from the subject are analyzed again, finding no trace of algal infection. The patient remains asymptomatic, and another fecal analysis performed 3 months later is normal.

EXAMPLE II

An elderly couple report fever, vomiting, and explosive diarrhea the morning after an evening celebration at a local Japanese restaurant. Since the couple prefer a vegetarian diet and ate only a Porphyra and kelp salad, the traditional suspect, poorly cooked seafood, was ruled out. Wet mount analysis of the fecal samples, show large numbers of a tiny, non-motile, unicellular green alga, Chlorella. The infection is diagnosed and treated by orally administering approximately 400 milligrams of bismuth in the form of bismuth subcitrate ("DeNol" sold by Brocades), in four equal doses daily for about 28 days. Thereafter, fecal, samples from the subject are analyzed again, finding no trace of algal infection.

EXAMPLE III

A Peace Corps volunteer diagnosed with AIDS, prepared for a temporary assignment working at an AIDS hospice in Peru. The job description describes a small village with sub-standard sanitation and water purification systems. The people of the village had recently experienced an outbreak of dysentery attributed to the cyanobacterium, *Microcystis aeruginosa*. Before leaving for his new assignment, clinical results show no evidence of cyanobacterial infection. Before departure, the subject is given approximately 800 milligrams of bismuth, in the form bismuth subgalate (Devrom®, sold by The Parthenon Company, Inc.), in four equal doses daily for about 21 days. Upon returning to the U.S., approximately 30 days after the initial clinical analysis, the subject remains asymptomatic. Fecal samples from the subject are analyzed and no evidence of a cyanobacterial infection is found.

What is claimed is:

1. A method for treatment of a human or lower animal subject having a gastrointestinal disorder caused or mediated by one or more organisms selected from the group consisting of algae, cyanobacteria, and combinations thereof, comprising administering to the subject from about 50 milligrams to about 5000 milligrams of bismuth, per day, for from about 1 to 56 days.

2. The method of claim 1 wherein the bismuth is administered at a level of from about 50 milligrams to about 2500 milligrams, per day.

3. The method of claim 1 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

4. The method of claim 1 wherein the organisms are cyanobacteria selected from the group consisting of *Microcystis aeruginosa*, *Aphanizomenon flos-aquae*, and *Anabaena flos-aqua*, and combinations thereof.

5. A method for prevention in a human or lower animal subject in need thereof, of a gastrointestinal disorder caused or mediated by one or more one or more organisms selected from the group consisting of algae, cyanobacteria, and combinations thereof, comprising administering to the subject from about 50 milligrams to about 5000 milligrams of bismuth, per day, for from about 1 to 21 days.

6. The method of claim 5 wherein the bismuth is administered at a level of from about 50 milligrams to about 2500 milligrams, per day.

7. The method of claim 5 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

8. The method of claim 5 wherein the organisms are algae and cyanobacteria selected from the group consisting of Chlorella, Chlorococcum, *Microcystis aeruginosa*, *Anabaena flos-aqua*, *Aphanizomenon flos-aquae*, and combinations thereof.

* * * * *

UNITED STATES PATENT AND TRADEMARK OFFICE
CERTIFICATE OF CORRECTION

PATENT NO. : 5,702,729
DATED : December 30, 1997
INVENTOR(S) : JAMESINA ANNE FITZGERALD It is certified that error appears in the above-identified patent and that said Letters Patent is hereby corrected as shown below:

Column 1, line 39, "derailed" should be --detailed--.

Column 2, line 21, "Cyanobaeteria" should be --Cyanobacteria--.

Column 2, line 39, "*multiseries*" should be --maltiseries--.

Column 2, line 43, "Rhoclymenia" should be --Rhodymenia--.

Column 3, line 36, "titrate" should be --citrate--.

Column 3, line 38, "titrate" should be --citrate--.

Signed and Sealed this

Sixth Day of October, 1998

*Attest:*

BRUCE LEHMAN

*Attesting Officer*   Commissioner of Patents and Trademarks